United States Patent
Iwahara

(10) Patent No.: US 6,653,513 B1
(45) Date of Patent: Nov. 25, 2003

(54) PROCESS FOR PRODUCING BISPHENOL A

(75) Inventor: Masahiro Iwahara, Tokuyama (JP)

(73) Assignee: Idemitsu Petrochemical Co., Ltd., Tokyo (JP)

( * ) Notice: Subject to any disclaimer, the term of this patent is extended or adjusted under 35 U.S.C. 154(b) by 0 days.

(21) Appl. No.: 09/582,085

(22) PCT Filed: Sep. 28, 1999

(86) PCT No.: PCT/JP99/05280

§ 371 (c)(1),
(2), (4) Date: Jun. 22, 2000

(87) PCT Pub. No.: WO00/23408

PCT Pub. Date: Apr. 27, 2000

(30) Foreign Application Priority Data

Oct. 22, 1998 (JP) ............................................. 10-300866

(51) Int. Cl.[7] ............................................. C07C 37/20
(52) U.S. Cl. ........................................................ 568/728
(58) Field of Search .................................. 568/724, 728

(56) References Cited

U.S. PATENT DOCUMENTS 4,859,803 A * 8/1989 Shaw ........................... 568/727

FOREIGN PATENT DOCUMENTS

| CA | 734972 | * | 5/1966 |
|----|--------|---|--------|
| GB | 1185102 | * | 3/1970 |
| GB | 1410750 | * | 10/1975 |
| JP | 5-294867 | * | 11/1993 |
| JP | 5-345737 | * | 12/1993 |
| JP | 6-32755 | * | 2/1994 |
| JP | 6-107582 | * | 4/1994 |
| JP | 6-92889 | * | 5/1994 |
| JP | 6-321834 | * | 11/1994 |
| JP | 6-343879 | * | 12/1994 |
| SU | 701986 | * | 12/1979 |

* cited by examiner

Primary Examiner—Michael L. Shippen
(74) Attorney, Agent, or Firm—Oblon, Spivak, McClelland, Maier & Neustadt, P.C.

(57) ABSTRACT

Provided is a process for producing bisphenol A having a stable color tone at a high temperature and free from coloration, which comprises reacting phenol with acetone in the presence of an acid ion-exchange resin as a catalyst and an alkyl mercaptan as a cocatalyst, wherein a concentration of an organosulfur compound in a crystallization starting material obtained by conducting the reaction under conditions that a reaction temperature is between 60 and 100° C., a phenol to acetone molar ratio is between 6 and 13 and an acetone to alkyl mercaptan molar ratio is between 13 and 25, distilling off unreacted acetone, by-product water and the alkyl mercaptan as the cocatalyst and further distilling off excess phenol is measured, and maintained at 200 weight ppm or less.

20 Claims, No Drawings

PROCESS FOR PRODUCING BISPHENOL A

TECHNICAL FIELD

The present invention relates to a process for producing bisphenol A having a stable color tone.

BACKGROUND ART

Bisphenol A[2,2-bis(4-hydroxyphenyl)propane] has been known to be an important compound as a starting material of engineering plastics such as a polycarbonate resin and a polyarylate resin and an epoxy resin, and the demand for it has been increased in recent years. Especially when bisphenol A is used as a starting material of a polycarbonate resin, it is required that its color tone is stable at a high temperature and coloration does not occur.

It has been known that bisphenol A is produced by condensing excess phenol and acetone in the presence of an acid catalyst and as required, a cocatalyst of a sulfur compound such as an alkyl mercaptan. In this method, various attempts have been made so far to improve the color tone of bisphenol A.

For example, JP-B-40-19333 discloses a method in which bisphenol A having an improved color tone is obtained by adding oxalic acid or citric acid to a mixture of phenol, water and bisphenol A, and then subjecting the resulting mixture to distillation. Further, JP-B-47-43937 discloses a method in which thioglycolic acid, glycolic acid or polyphosphoric acid is added. JP-A-2-231444 discloses a method in which lactic acid, malic acid or glyceric acid is added. Still further, JP-B7-78030describes a method in which an aliphatic carboxylic acid is added, and phenol is removed from a phenol adduct in vacuo by evaporation. However, these methods were all intricate requiring the addition of the third substance. Further, the effect of improving the color tone was still unsatisfactory.

Under these circumstances, the present invention has been made. It is an object of the present invention to provide a process for producing bisphenol A having a stable color tone at a high temperature and free from coloration.

DISCLOSURE OF THE INVENTION

The present inventors have assiduously conducted investigations, and have consequently found that when phenol is reacted with acetone using an acid ion-exchange resin as a catalyst and analkyl mercaptan as a cocatalyst, a concentration of an organosulfur compound in a crystallization starting material when recovering an adduct of bisphenol A and phenol as a crystal from a concentrate of the reaction mixture influences the color tone of bisphenol A at a high temperature. This finding has led to the completion of the present invention.

That is, the present invention is to provide a process for producing bisphenol A, which comprises reacting phenol with acetone in the presence of an acid ion-exchange resin as a catalyst and an alkyl mercaptan as a cocatalyst, wherein a concentration of an organosulfur compound in a crystallization starting material obtained by conducting the reaction under conditions that a reaction temperature is between 60 and 100° C., a phenol to acetone molar ratio is between 6 and 13 and an acetone to alkyl mercaptan molar ratio is between 13 and 25, distilling off unreacted acetone, by-product water and the alkyl mercaptan as the cocatalyst and further distilling off excess phenol is maintained at 200 weight ppm or less.

BEST MODE FOR CARRYING OUT THE INVENTION

The present invention is described in detail below.

In the present invention, bisphenol A is produced by reacting excess phenol with acetone in the presence of an acid ion-exchange resin as a catalyst and an alkyl mercaptan as a cocatalyst.

As the acid ion-exchange resin, for example, a sulfonic acid cation-exchange resin is preferably used. Specific examples thereof include a sulfonated styrene divinylbenzene copolymer, a sulfonated crosslinked styrene polymer, a phenol formaldehyde-sulfonic acid resin and a benzene formaldehyde-sulfonic acid resin. These may be used either singly or in combination.

As the alkyl mercaptan used as the cocatalyst, a mercaptan containing an alkyl group having from 1 to 10 carbon atoms is preferable. Specific examples thereof include methyl mercaptan, ethyl mercaptan, propyl mercaptan, octyl mercaptan and cyclohexyl mercaptan. Of these, ethyl mercaptan is especially preferable. These alkyl mercaptans may be used either singly or in combination.

The reaction method is not particularly limited. A fixed bed continuous reaction or batchwise reaction is preferable. The fixed bed continuous reaction is especially preferable. When the fixed bed continuous reaction is carried out, a liquid hourly space velocity (LHSV) is usually between 0.2 and 30 $hr^{-1}$, preferably between 0.5 and 6 $hr^{-1}$. When LHSV is less than $0.2hr^{-1}$, the productivity of bisphenol A is sometimes decreased. When it is more than 30 $hr^{-1}$, the reactivity is sometimes decreased.

The reaction temperature has to be between 60 and 100° C. When it is less than 60° C., a phenol phase is sometimes solidified. Further, when it exceeds 100° C., deterioration of the acid ion-exchange resin is increased undesirably. The range of from 65 to 95° C. is preferable.

The phenol to acetone molar ratio has to be between 6 and 13. When it is less than 6, the concentration of the organosulfur compound in the crystallization starting material to be described later exceeds 200 weight ppm. Further, when it exceeds 13, the reaction rate is decreased, and the amount of phenol recovered is increased undesirably. The range of from 8 to 12 is preferable.

The reaction has to be conducted under a condition that the acetone to alkyl mercaptan molar ratio is between 13 and 25. When it is less than 13, the concentration of the organosulfur compound in the crystallization starting material to be described later exceeds 200 weight ppm. Further, when it exceeds 25, the reaction rate is decreased, and the reaction selectivity is decreased undesirably. The range of from 17 to 22 is preferable.

The reaction mixture contains, other than bisphenol A, by-products such as unreacted phenol, unreacted acetone, a catalyst, by-product water, an alkylmercaptan, anorganosulfur compound other than the alkyl mercaptan and a coloring matter. Accordingly, the post-treatment is required to produce bisphenol A to comply with the object of the present invention.

Next, with respect to the reaction mixture, the catalyst is removed by separation through filtration in the batchwise reaction. The residual liquid components, namely, unreacted acetone, by-product water and the alkyl mercaptan are removed by vacuum distillation. When a distillation column is used, unreacted acetone, water and the alkyl mercaptan are removed from the top of the column, and the liquid mixture containing bisphenol A and phenol is obtained from the bottom of the column.

When phenol and acetone are reacted in the fixed bed continuous reaction, removal of the catalyst is unnecessary. The liquid components discharged from the reaction vessel are treated in the above-mentioned manner.

The vacuum distillation can be conducted at a temperature of from 70 to 180° C. and a pressure of from 50 to 600 torr. When unreacted acetone, by-product water and the alkyl mercaptan are removed using the distillation column, unreacted phenol is formed azeotropically, and a part thereof is removed outside the system from the top of the column.

Unreacted acetone, by-product water and the alkyl mercaptan as the cocatalyst are distilled off from the reaction mixture in this manner.

From the solution obtained by removing these substances from the reaction mixture, phenol is further distilled off through vacuum distillation to concentrate bisphenol A. This concentrated residue becomes a crystallization starting material in the next step.

The concentration conditions are not particularly limited. The concentration is usually conducted at a temperature of from 100 to 170° C. and a pressure of from 40 to 500 torr. When the temperature is lower than 100° C., a high degree of vacuum is required. When it is higher than 170° C., an extra step of removal of heat is required in the subsequent crystallization step. Further, the concentration of bisphenol A in the concentrated residue is preferably between 20 and 50% by weight, more preferably between 20 and 40% by weight. When this concentration is less than 20% by weight, the recovery of bisphenol A is sometimes low. When it exceeds 50% by weight, the slurry after crystallization is sometimes hard to transfer.

In the present invention, the concentration of the organosulfur compound in this concentrated residue is measured. This concentration has to be 200 weight ppm or less. When it exceeds 200 weight ppm, the color tone of bisphenol A obtained worsens. The concentration of the organosulfur compound can be measured by a known method such as gas chromatography or with a known equipment such as a total sulfur analyzer.

Main examples of the organosulfur compound include byproducts derived from mercaptan, such as a dialkyl disulfide, thioacetal, a mercaptan adduct of an acetone dimer and a reaction product of phenol, acetone and mercaptan.

Bisphenol A having a stable color tone at a high temperature and free from coloration can be obtained by making the concentration of this organosulfur compound 200 ppm or less. That is, it is possible to judge the off-specification of bisphenol A as a product and to judge the time of the catalyst exchange. The preferable index of the concentration of the organosulfur compound is 50 weight ppm or less.

The present invention relates to a process for producing bisphenol A in which the concentration of the organosulfur compound is made 200 weight ppm or less without using the third substances.

The concentrated residue is cooled to between 40 and 700° C. Then, the adduct of bisphenol A and phenol (hereinafter abbreviated as "phenol adduct") is crystallized to form a slurry. The cooling can be conducted, for example, by removal of heat through evaporation of water added to an external heat exchanger or a crystallization device.

Subsequently, the concentrated residue as a slurry is separated into phenol adduct crystals and a crystallization mother liquor containing reaction by-products through filtration or centrifugation. It is possible that this crystallization mother liquor is recycled into a reaction vessel directly or partially or a part or the whole thereof is decomposed with an alkali and recovered as phenol and isopropenyl phenol. Further, it is also possible that a part or the whole thereof is isomerized and recycled into a crystallization starting material (refer to JP-A-6-321834).

When the above-obtained crystals of the adduct of bisphenol A and phenol are heated at from 100 to 160° C., a liquid mixture is formed. Bisphenol A can be recovered in a molten state by removing phenol from this liquid mixture through vacuum distillation. The vacuum distillation is usually conducted at a temperature of from 150 to 190° C. and a pressure of from 10 to 100 torr. Further, residual phenol can also be removed through steam stripping.

Bisphenol A in the molten state is formed into droplets with a pulverization unit such as a spray drier, and the droplets are cooled, and solidified to form a product. The droplets are provided through spraying or scattering, and cooled and solidified with nitrogen or air, etc.

EXAMPLES

The present invention is illustrated more specifically by referring to the following Examples. However, the present invention is not limited to these Examples.

Example 1

A packed-bed-type reaction vessel having an inner diameter of 20 mm and a height of 1,500 mm was charged with a sulfonic acid ion-exchange resin (Diaion-SK104H, made by Mitsubishi Chemical Industries Ltd.). The reaction temperature was maintained at 80° C., and phenol, acetone and ethyl mercaptan were charged from the inlet of the reaction vessel at a phenol to acetone molar ratio of 10 and an acetone to ethyl mercaptan molar ratio of 20 with LHSV of 1 $hr_{-1}$ to conduct the reaction. When the acetone recovery became 75%, the reaction solution was collected. Unreacted acetone and a part of excess phenol were distilled off from the reaction solution at a temperature of 172° C. and a pressure of 500 torr. Further, excess phenol was distilled off at a temperature of 134° C. and a pressure of 118 torr to concentrate bisphenol A to 40% by weight. This concentrate (crystallization starting material) contained 20 weight ppm of the organosulfur compound. This concentrate was cooled to 43° C. to crystallize the phenol adduct, and the solid-liquid separation was then conducted. From the phenol adduct crystals, phenol was removed at a temperature of 170° C. and a pressure of 30 torr to obtain bisphenol A. Subsequently, 90% of the crystallization mother liquor was subjected to an isomerization reaction at a reaction temperature of 80° C. in the presence of a sulfonic acid ion-exchange resin (Diaion-SK104H, made by Mitsubishi Chemical Industries, Ltd.) as a catalyst, and then recycled as a crystallization starting material. Remaining 10% of the crystallization mother liquor was discharged by recovering phenol. Even when 90% of the crystallization mother liquor was treated with the abovementioned method and recycled, the concentration of the organosulfur compound did not exceed 200 weight ppm.

The color tone of the resulting bisphenol A was visually evaluated with an APHA standard solution by heating in an air atmosphere at 220° C. for 30 minutes. As a result, the color tone was 10 APHA, and good.

Example 2

Bisphenol A was produced in the same manner as in Example 1 except that the acetone to ethyl mercaptan molar ratio was changed to 17. The concentration of the organosulfur compound in the crystallization starting material was 25 weight ppm, and the color tone of the resulting bisphenol A was 10 APHA, and good.

Example 3

Bisphenol A was produced in the same manner as in Example 1 except that the reaction temperature was changed to 85° C., the acetone to ethyl mercaptan molar ratio to 22 respectively. The concentration of the organosulfur compound in the crystallization starting material was 18 weight ppm, and the color tone of the resulting bisphenol A was 10 APHA, and good.

Example 4

Bisphenol A was produced in the same manner as in Example 1 except that the reaction temperature was changed to 70° C., the phenol to acetone molar ratio to 9 and the acetone to ethyl mercaptan molar ratio to 18 respectively. The concentration of the organosulfur compound in the crystallization starting material was 38 weight ppm, and the color tone of the resulting bisphenol A was 10 APHA, and good.

Comparative Example 1

Bisphenol A was produced in the same manner as in Example 1 except that the reaction temperature was changed to 85° C., the phenol to acetone molar ratio to 6 and the acetone to ethyl mercaptan molar ratio to 10 respectively. The concentration of the organosulfur compound in the crystallization starting material was 247 weight ppm, and the color tone of the resulting bisphenol A was 30 APHA, so that no good color tone was obtained.

Comparative Example 2

Bisphenol A was produced in the same manner as in Example 1 except that the reaction temperature was changed to 95° C., the phenol to acetone molar ratio to 5 and the acetone to ethyl mercaptan molar ratio to 8 respectively. The concentration of the organosulfur compound in the crystallization starting material was 386 weight ppm, and the color tone of the resulting bisphenol A was 35 APHA, so that no good color tone was obtained.

Comparative Example 3

Bisphenol A was produced in the same manner as in Example 1 except that the reaction temperature was changed to 90° C., the phenol to acetone molar ratio to 4 and the acetone to ethyl mercaptan molar ratio to 7 respectively. The concentration of the organosulfur compound in the crystallization starting material was 523 weight ppm, and the color tone of the resulting bisphenol A was 45 APHA, so that no good color tone was obtained.

Industrial Utility Field

In accordance with the present invention, the concentration of the organosulfur compound in the crystallization starting material can be made 200 weight ppm or less. Accordingly, bisphenol A having a stable color tone at a high temperature and free from coloration can be produced.

Further, since it is unnecessary to add the third substances mentioned in the description of the related art, a simple process can be employed.

Still further, it is possible to judge the off-specification of bisphenol A as a product and the time of the catalyst exchange using the concentration of the organosulfur compound in the crystallization starting material as an index. Accordingly, bisphenol A having a stable color tone at a high temperature and free from coloration can stably be produced.

What is claimed is:

1. A process for producing bisphenol A, which comprises:

reacting phenol with acetone in the presence of an acid ion-exchange resin as a catalyst and a cocatalyst consisting essentially of an alkyl mercaptan, wherein a concentration of an organosulfur compound in a crystallization starting material obtained by conducting the reaction under conditions that a reaction temperature is between 60 and 100° C., a phenol to acetone molar ratio is between 6 and 13 and an acetone to alkyl mercaptan molar ratio is between 13 and 25, distilling off unreacted acetone, by-product water and the alkyl mercaptan as the cocatalyst and further distilling off excess phenol is maintained at 200 weight ppm or less;

separating the crystallization starting material into phenol adduct crystals and a crystallization mother liquor; and recycling the crystallization mother liquor, wherein a part or the whole of the crystallization mother liquor is isomerized and recycled into the crystallization starting material.

2. The process for producing bisphenol A as claimed in claim 1, wherein the acid ion-exchange resin is a sulfonic acid cation-exchange resin.

3. The process for producing bisphenol A as claimed in claim 1, wherein the alkyl mercaptan is ethyl mercaptan.

4. The process for producing bisphenol A as claimed in claim 2, wherein the alkyl mercaptan is ethyl mercaptan.

5. The process for producing bisphenol A as claimed in claim 1, wherein the reaction temperature is from 65 and 95° C.

6. The process for producing bisphenol A as claimed in claim 1, wherein the phenol to acetone molar ratio is from 8 and 12.

7. The process for producing bisphenol A as claimed in claim 1, wherein the acetone to alkyl mercaptan molar ratio is from 17 and 22.

8. The process for producing bisphenol A as claimed in claim 1, wherein the concentration of organosulfur compound in the crystallization starting material is 50 weight ppm or less.

9. The process for producing bisphenol A as claimed in claim 2, wherein the reaction temperature is from 65 and 95° C.

10. The process for producing bisphenol A as claimed in claim 2, wherein the phenol to acetone molar ratio is from 8 and 12.

11. The process for producing bisphenol A as claimed in claim 2, wherein the acetone to alkyl mercaptan molar ratio is from 17 and 22.

12. The process for producing bisphenol A as claimed in claim 2, wherein the concentration of organosulfur compound in the crystallization starting material is 50 weight ppm or less.

13. The process for producing bisphenol A as claimed in claim 3, wherein the reaction temperature is from 65 and 95° C.

14. The process for producing bisphenol A as claimed in claim 3, wherein the phenol to acetone molar ratio is from 8 and 12.

15. The process for producing bisphenol A as claimed in claim 3, wherein the acetone to alkyl mercaptan molar ratio is from 17 and 22.

16. The process for producing bisphenol A as claimed in claim 3, wherein the concentration of organosulfur compound in the crystallization starting material is 50 weight ppm or less.

17. The process for producing bisphenol A as claimed in claim 4, wherein the reaction temperature is from 65 and 95° C.

18. The process for producing bisphenol A as claimed in claim 4, wherein the phenol to acetone molar ratio is from 8 and 12.

19. The process for producing bisphenol A as claimed in claim 4, wherein the acetone to alkyl mercaptan molar ratio is from 17 and 22.

20. The process for producing bisphenol A as claimed in claim 4, wherein the concentration of organosulfur compound in the crystallization starting material is 50 weight ppm or less.

\* \* \* \* \*